(12) United States Patent
Clarke

(10) Patent No.: US 9,212,367 B2
(45) Date of Patent: Dec. 15, 2015

(54) METHODS FOR IMPROVING RECOMBINANT PROTEIN EXPRESSION

(75) Inventor: Howard R. Clarke, Friday Harbor, WA (US)

(73) Assignee: CMC ICOS BIOLOGICS, INC., Bothell, WA (US)

( * ) Notice: Subject to any disclaimer, the term of this patent is extended or adjusted under 35 U.S.C. 154(b) by 726 days.

(21) Appl. No.: 13/390,297

(22) PCT Filed: Aug. 6, 2010

(86) PCT No.: PCT/US2010/044693
§ 371 (c)(1),
(2), (4) Date: May 7, 2012

(87) PCT Pub. No.: WO2011/017606
PCT Pub. Date: Feb. 10, 2011

(65) Prior Publication Data
US 2012/0214203 A1   Aug. 23, 2012

Related U.S. Application Data

(60) Provisional application No. 61/231,906, filed on Aug. 6, 2009.

(51) Int. Cl.
*C12N 15/67*   (2006.01)
*C12N 9/06*   (2006.01)

(52) U.S. Cl.
CPC ............... *C12N 15/67* (2013.01); *C12N 9/003* (2013.01)

(58) Field of Classification Search
None
See application file for complete search history.

(56) References Cited

U.S. PATENT DOCUMENTS

| | | | |
|---|---|---|---|
| 4,704,362 A | | 11/1987 | Itakura et al. |
| 5,733,779 A | * | 3/1998 | Reff ............................ 435/320.1 |
| 5,795,737 A | | 8/1998 | Seed et al. |
| 5,888,809 A | | 3/1999 | Allison |
| 2004/0092009 A1 | * | 5/2004 | Draghia-Akli et al. ..... 435/320.1 |
| 2005/0106580 A1 | * | 5/2005 | Enenkel et al. ................... 435/6 |
| 2005/0196865 A1 | * | 9/2005 | Frazer ........................... 435/456 |
| 2006/0154369 A1 | | 7/2006 | Kuo et al. |
| 2006/0172382 A1 | * | 8/2006 | Otte et al. .................... 435/69.1 |
| 2007/0298503 A1 | * | 12/2007 | Lathrop et al. .................. 436/34 |
| 2008/0118530 A1 | | 5/2008 | Kew et al. |
| 2008/0187953 A1 | | 8/2008 | Enenkel et al. |
| 2008/0293105 A1 | | 11/2008 | Allison |

FOREIGN PATENT DOCUMENTS

| | | |
|---|---|---|
| EP | 1591523 A1 | 11/2005 |
| WO | WO-2004/070030 A1 | 8/2004 |
| WO | WO-2006/042156 A2 | 4/2006 |

OTHER PUBLICATIONS

Deer et al. High-level expression of proteins in mammalian cells using transcription regulatory sequences from the Chinese Hamster EF-1alpha gene. Biotechnology Progress, vol. 20, No. 3, pp. 880-889, 2004.*
Struhl, K. Fundamentally different logic of gene regulation in eukaryotes and prokaryotes. Cell, vol. 98, pp. 1-4, Jul. 1999.*
Boycheva et al., Codon pairs in the genome of *Escherichia coli*, *Bioinformatics*, 19(8):987-98 (2003).
Bulmer, Codon usage and secondary structure of MS2 phage RNA, *Nucleic Acids Res.*, 17(5):1839-43 (1989).
Burns et al. Modulation of poliovirus replicative fitness in HeLa cells by deoptimization of synonymous codon usage in the capsid region, *J. Virol.*, 80: 3259 (2006).
Carlini et al., In vivo introduction of unpreferred synonymous codons into the Drosophila Adh gene results in reduced levels of ADH protein, *Genetics*, 163(1):239-43 (2003).
Coleman et al., Virus attenuation by genome-scale changes in codon pair bias, *Science*, 320:1784-7 (2008).
Griswold et al., Effects of codon usage versus putative 5'-mRNA structure on the expression of Fusarium solani cutinase in the *Escherichia coli* cytoplasm, *Protein Expr. Purif.*, 27(1):134-42 (2003).
Gruber et al., The Vienna RNA websuite, *Nucleic Acids Res.*, 36(Web Server issue):W70-4 (2008).
Gurvich et al., Expression levels influence ribosomal frameshifting at the tandem rare arginine codons AGG_AGG and AGA_AGA in *Escherichia coli, J. Bacteriol.*, 187(12):4023-32 (2005).
Gustafsson et al., Codon bias and heterologous protein expression, *Trends Biotechnol.*, 22(7):346-53 (2004).
Gutman et al., Nonrandom utilization of codon pairs in *Escherichia coli, Proc. Natl. Acad. Sci. USA*, 86(10):3699-703 (1989).
Hall et al., A role for mRNA secondary structure in the control of translation initiation, *Nature*, 295(5850):616-8 (1982).
Holler et al., HIV1 integrase expressed in *Escherichia coli* from a synthetic gene, HIV1 integrase expressed in *Excherichia coli* from a synthetic gene, *Gene*, 136(1-2):323-8 (1993).
Ikemura, Codon usage and tRNA content in unicellular and multicellular organisms, *Mol. Biol. Evol.*, 2(1):13-34 (1985).
Ikemura, Correlation between the abundance of *Escherichia coli* transfer RNAs and the occurrence of the respective codons in its protein genes, *J. Mol. Biol.*, 146(1):1-21 (1981).
Ikemura, Correlation between the abundance of *Escherichia coli* transfer RNAs and the occurrence of the respective codons in its protein genes: a proposal for a synonymous codon choice that is optimal for the *E. coli* translational system, *J. Mol. Biol.*, 151(3):389-409 (1981).
International Preliminary Report on Patentability, corresponding International Application No. PCT/US2010/044693, dated Feb. 7, 2012.
International Search Report and Written Opinion, corresponding International Application No. PCT/US10/44693, mailing date Dec. 6, 2010.
Kaufman et al., Improved vectors for stable expression of foreign genes in mammalian cells by use of the untranslated leader sequence from EMC virus, *Nucleic Acids Res.*, 19(16):4485-90 (1991).

(Continued)

Primary Examiner — Jennifer Dunston
(74) Attorney, Agent, or Firm — Marshall, Gerstein & Borun LLP

(57) ABSTRACT

Materials and methods are provided which allowed for increased expression of a transfected gene of interest in a recombinant host cell.

1 Claim, 8 Drawing Sheets

(56) References Cited

OTHER PUBLICATIONS

Kozak, Regulation of translation via mRNA structure in prokaryotes and eukaryotes, *Gene*, 361:13-37 (2005).

Kudla et al., Coding-sequence determinants of gene expression in *Escherichia coli*, *Science*, 324(5924):255-8 (2009).

Lowe et al., tRNAscan-SE: a program for improved detection of transfer RNA genes in genomic sequence, *Nucleic Acids Res.*, 25(5):955-64 (1997).

Maniatis et al., Molecular Cloning. A Laboratory Manual, New York: Cold Spring Harbor Laboratory (1982), pp. v-x.

Mesbah et al., Precise measurement of the G+C content of deoxyribonucleic acid by high-performance liquid chromatography, *IJSEM*, 39(2):159-67 (1989).

Mueller et al., Reduction of the rate of poliovirus protein synthesis through large-scale codon deoptimization causes attenuation of viral virulence by lowering specific infectivity, J. Virol., 80(19):9687-96 (2006).

Pelletier et al., The involvement of mRNA secondary structure in protein synthesis, *Biochem. Cell Biol.*, 65(6):576-81 (1987).

Rosenberg et al., Effects of consecutive AGG codons on translation in *Escherichia coli*, demonstrated with a versatile codon test system, *J. Bacteriol.*, 175(3):716-22 (1993).

Sharp et al., The codon Adaptation Index—a measure of directional synonymous codon usage bias, and its potential applications, *Nucleic Acids Res.*, 15(3):1281-95 (1987).

Smith et al., tRNA-tRNA interactions within cellular ribosomes, *Proc. Natl. Acad. Sci. USA*, 86(12):4397-401 (1989).

Sueoka et al., DNA G+C content of the third codon position and codon usage biases of human genes, *Gene*, 261(1):53-62 (2000).

Watson, Molecular Biology of the Gene, Fourth Edition, The Benjamin/Cummings Publishing Company (1989), pp. x-xxix.

Westwood et al., Improved recombinant protein yield using a codon deoptimized DHFR selectable marker in a CHEF1 expression plasmid, *Biotechnol. Prog.*, 26(6):1558-66 (2010).

Zhang et al., Low-usage codons in *Escherichia coli*, yeast, fruit fly and primates, *Gene*, 105(1):61-72 (1991).

* cited by examiner

Figure 1

A) *Mus musculus* DHFR polynucleotide

```
ATG GTT CGA CCA TTG AAC TGC ATC GTC GCC GTG TCC CAA AAT ATG GGG ATT GGC AAG AAC GGA
GAC CTA CCC TGG CCT CCG CTC AGG AAC GAG TTC AAG TAC TTC CAA AGA ATG ACC ACA ACC TCT
TCA GTG GAA GGT AAA CAG AAT CTG GTG ATT ATG GGT AGG AAA ACC TGG TTC TCC ATT CCT GAG
AAG AAT CGA CCT TTA AAG GAC AGA ATT AAT ATA GTT CTC AGT AGA GAA CTC AAA GAA CCA CCA
CGA GGA GCT CAT TTT CTT GCC AAA AGT TTG GAT GAT GCC TTA AGA CTT ATT GAA CAA CCG GAA
TTG GCA AGT AAA GTA GAC ATG GTT TGG ATA GTC GGA GGC AGT TCT GTT TAC CAG GAA GCC ATG
AAT CAA CCA GGC CAC CTC AGA CTC TTT GTG ACA AGG ATC ATG CAG GAA TTT GAA AGT GAC ACG
TTT TTC CCA GAA ATT GAT TTG GGG AAA TAT AAA CTT CTC CCA GAA TAC CCA GGC GTC CTC TCT
GAG GTC CAG GAG GAA AAA GGC ATC AAG TAT AAG TTT GAA GTC TAC GAG AAG AAA GAC TAA
```

B) *Mus musculus* DHFR polypeptide

```
MVRPLNCIVAVSQNMGIGKNGDLPWPPLRNEFKYFQRMTTTSSVEGKQNLVIMGRKTWFS
IPEKNRPLKDRINIVLSRELKEPPRGAHFLAKSLDDALRLIEQPELASKVDMVWIVGGSS
VYQEAMNQPGHLRLFVTRIMQEFESDTFFPEIDLGKYKLLPEYPGVLSEVQEEKGIKYKF
EVYEKKD-
```

Figure 2

```
>cr dhfr
ATG GTT CGA CCG CTT AAC TGC ATA GTA GCA GTA TCA CAA AAC ATG GGG ATA GGG AAA AAT GGG
GAT CTT CCG TGG CCG CCG TTG CGT AAC GAA TTC AAA TAC TTC CAA CGT ATG ACT ACT ACT TCA
TCA GTA GAA GGG AAA CAA AAC CTT GTA ATA ATG GGG CGT AAA ACA TGG TTC TCA ATA CCG GAA
AAA AAC CGT CCG CTT AAA GAC CGT ATA AAC ATA GTA CTT TCA CGT GAA CTT AAA GAA CCG CCG
CGT GGG GCA CAT TTT CTT GCA AAA TCA CTT GAC GAC GCA CTT CGT CTT ATA GAA CAA CCG GAA
CTT GCA TCA AAA GTA GAC ATG GTT TGG ATA GTA GGG GGG TCA TCA GTA TAC CAA GAA GCA ATG
AAC CAA CCG GGG CAC CTT CGT CTT TTC GTA ACT CGT ATA ATG CAA GAA TTC GAA TCA GAC ACT
TTC TTC CCG GAA ATA GAC CTT GGG AAA TAC AAA CTT CTT CCG GAA TAC CCG GGG GTA TTG TCA
GAA GTA CAA GAA GAA AAA GGG ATA AAA TAC AAA TTC GAA GTA TAC GAA AAA AAA GAC TAG
>wst dhfr
ATG GTT CGA CCG CTA AAC TGC ATA GTA GCG GTA TCG CAA AAC ATG GGG ATA GGG AAA AAT GGG
GAC TTA CCG TGG CCG CCG TTA CGA AAC GAA TTC AAA TAC TTC CAA CGT ATG ACG ACG ACG TCG
TCG GTA GAA GGG AAA CAA AAC CTA GTA ATA ATG GGG CGT AAA ACG TGG TTT TCG ATA CCG GAA
AAA AAC CGT CCG CTA AAA GAC CGT ATA AAC ATA GTA CTA TCG CGT GAA CTA AAA GAA CCG CCG
CGT GGG GCG CAT TTT TTA GCG AAA TCG CTA GAC GAC GCG CTA CGT CTA ATA GAA CAA CCG GAA
CTA GCG TCG AAA GTA GAC ATG GTT TGG ATA GTA GGG GGG TCG TCG GTA TAT CAA GAA GCG ATG
AAC CAA CCG GGG CAC TTA CGT TTA TTC GTA ACG CGA ATA ATG CAA GAA TTC GAA TCG GAC ACG
TTC TTC CCG GAA ATA GAC CTA GGG AAA TAC AAA CTA CTA CCG GAA TAC CCG GGG GTA CTA TCG
GAA GTA CAA GAA GAA AAA GGG ATA AAA TAC AAA TTC GAA GTA TAC GAA AAA AAA GAC TAG
```

Figure 3

```
>wt dhfr        #1    ATG GTT CGA CCA TTG AAC TGC ATC GTC GCC GTG TCC CAA AAT ATG GGG ATT GGC AAG AAC GGA
>cr dhfr        #1    ATG GTT CGA CCG CTT AAC TGC ATA GTA GCA GTA TCA CAA AAC ATG GGG ATA GGG AAA AAT GGG
>wst dhfr       #1    ATG GTT CGA CCG CTA AAC TGC ATA GTA GCG GTA TCG CAA AAC ATG GGG ATA GGG AAA AAT GGG
                      ..........................................................................
Contig[0001]    #1    ATG GTT CGA CCG CTD AAC TGC ATA GTA GCV GTA TCV CAA AAC ATG GGG ATA GGG AAA AAT GGG
                       *   *   *   *       *   *   *   *       *       *   *       *       *   *

>wt dhfr        #64   GAC CTA CCC TGG CCT CCG CTC AGG AAC GAG TTC AAG TAC TTC CAA AGA ATG ACC ACA ACC TCT
>cr dhfr        #64   GAT CTT CCG TGG CCG CCG TTG CGT AAC GAA TTC AAA TAC TTC CAA CGT ATG ACT ACT ACT TCA
>wst dhfr       #64   GAC TTA CCG TGG CCG CCG TTA CGA AAC GAA TTC AAA TAC TTC CAA CGT ATG ACG ACG ACG TCG
                      ..........................................................................
Contig[0001]    #64   GAC CTA CCG TGG CCG CCG TTV CGD AAC GAA TTC AAA TAC TTC CAA CGT ATG ACB ACD ACB TCD
                       *   *   *       *   *   *   *       *       *               *       *   *   *   *

>wt dhfr        #127  TCA GTG GAA GGT AAA CAG AAT CTG GTG ATT ATG GGT AGG AAA ACC TGG TTC TCC ATT CCT GAG
>cr dhfr        #127  TCA GTA GAA GGG AAA CAA AAC CTT GTA ATA ATG GGG CGT AAA ACA TGG TTC TCA ATA CCG GAA
>wst dhfr       #127  TCG GTA GAA GGG AAA CAA AAC CTA GTA ATA ATG GGG CGT AAA ACG TGG TTT TCG ATA CCG GAA
                      ..........................................................................
Contig[0001]    #127  TCA GTA GAA GGG AAA CAA AAC CTD GTA ATA ATG GGG CGT AAA ACV TGG TTC TCV ATA CCG GAA
                       *   *       *       *   *   *       *   *           *       *   *       *   *   *

>wt dhfr        #190  AAG AAT CGA CCT TTA AAG GAC AGA ATT AAT ATA GTT CTC AGT AGA GAA CTC AAA GAA CCA CCA
>cr dhfr        #190  AAA AAC CGT CCG CTT AAA GAC CGT ATA AAC ATA GTA CTT TCA CGT GAA CTT AAA GAA CCG CCG
>wst dhfr       #190  AAA AAC CGT CCG CTA AAA GAC CGT ATA AAC ATA GTA CTA TCG CGT GAA CTA AAA GAA CCG CCG
                      ..........................................................................
Contig[0001]    #190  AAA AAC CGT CCG CTA AAA GAC CGT ATA AAC ATA GTA CTH TCD CGT GAA CTH AAA GAA CCG CCG
                       *   *   *       *   *   *   *   *   *       *   *       *   *   *   *

>wt dhfr        #253  CGA GGA GCT CAT TTT CTT GCC AAA AGT TTG GAT GAT GCC TTA AGA CTT ATT GAA CAA CCG GAA
>cr dhfr        #253  CGT GGG GCA CAT TTT CTT GCA AAA TCA CTT GAC GAC GCA CTT CGT CTT ATA GAA CAA CCG GAA
>wst dhfr       #253  CGT GGG GCG CAT TTT TTA GCG AAA TCG CTA GAC GAC GCG CTA CGT CTA ATA GAA CAA CCG GAA
                      ..........................................................................
Contig[0001]    #253  CGT GGG GCD CAT TTT CTT GCV AAA TCD CTD GAC GAC GCV CTA CGT CTT ATA GAA CAA CCG GAA
                       *   *   *               *   *   ***  *   *           *   *   *   *   *

>wt dhfr        #316  TTG GCA AGT AAA GTA GAC ATG GTT TGG ATA GTC GGA GGC AGT TCT GTT TAC CAG GAA GCC ATG
>cr dhfr        #316  CTT GCA TCA AAA GTA GAC ATG GTT TGG ATA GTA GGG GGG TCA TCA GTA TAC CAA GAA GCA ATG
>wst dhfr       #316  CTA GCG TCG AAA GTA GAC ATG GTT TGG ATA GTA GGG GGG TCG TCG GTA TAT CAA GAA GCG ATG
                      ..........................................................................
Contig[0001]    #316  CTD GCA TCD AAA GTA GAC ATG GTT TGG ATA GTA GGG GGG TCD TCD GTA TAC CAA GAA GCV ATG
                       * *     * ***                                   *   *   *   *       *       *

>wt dhfr        #379  AAT CAA CCA GGC CAC CTC AGA CTC TTT GTG ACA AGG ATC ATG CAG GAA TTT GAA AGT GAC ACG
>cr dhfr        #379  AAC CAA CCG GGG CAC CTT CGT CTT TTC GTA ACT CGT ATA ATG CAA GAA TTC GAA TCA GAC ACT
>wst dhfr       #379  AAC CAA CCG GGG CAC TTA CGT TTA TTC GTA ACG CGA ATA ATG CAA GAA TTC GAA TCG GAC ACG
                      ..........................................................................
Contig[0001]    #379  AAC CAA CCG GGG CAC CTH CGT CTH TTC GTA ACD CGD ATA ATG CAA GAA TTC GAA TCD GAC ACG
                       *   *   *   *   *       *   *   *       *   *                       ***

>wt dhfr        #442  TTT TTC CCA GAA ATT GAT TTG GGG AAA TAT AAA CTT CTC CCA GAA TAC CCA GGC GTC CTC TCT
>cr dhfr        #442  TTC TTC CCG GAA ATA GAC CTT GGG AAA TAC AAA CTT CTT CCG GAA TAC CCG GGG GTA TTG TCA
>wst dhfr       #442  TTC TTC CCG GAA ATA GAC CTA GGG AAA TAC AAA CTA CTA CCG GAA TAC CCG GGG GTA CTA TCG
                      ..........................................................................
Contig[0001]    #442  TTC TTC CCG GAA ATA GAC CTD GGG AAA TAC AAA CTT CTH CCG GAA TAC CCG GGG GTA CTV TCD
                       *       *       *   *           *           *   *       *       *       *   *   *

>wt dhfr        #505  GAG GTC CAG GAG GAA AAA GGC ATC AAG TAT AAG TTT GAA GTC TAC GAG AAG AAA GAC TAA
>cr dhfr        #505  GAA GTA CAA GAA GAA AAA GGG ATA AAA TAC AAA TTC GAA GTA TAC GAA AAA AAA GAC TAG
>wst dhfr       #505  GAA GTA CAA GAA GAA AAA GGG ATA AAA TAC AAA TTC GAA GTA TAC GAA AAA AAA GAC TAG
                      ..........................................................................
Contig[0001]    #505  GAA GTA CAA GAA GAA AAA GGG ATA AAA TAC AAA TTC GAA GTA TAC GAA AAA AAA GAC TAG
                       *   *   *   *                           *                       *
```

Figure 7A
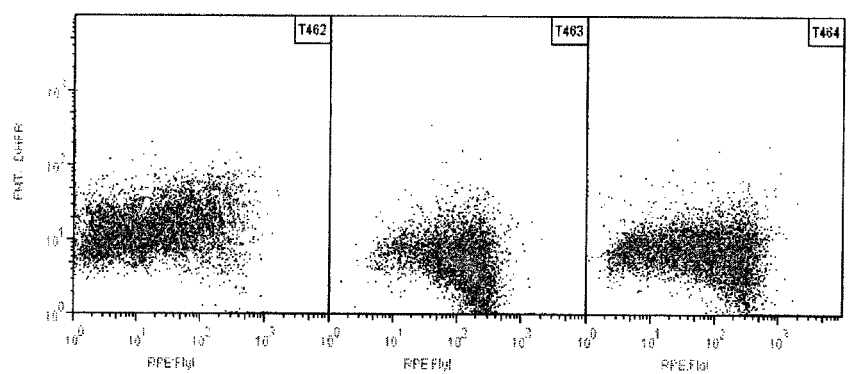
Figure 7B
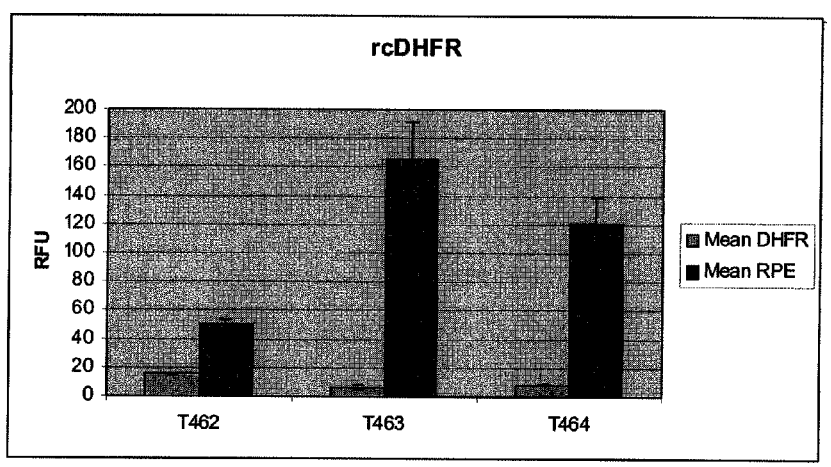
Figure 7

SEQUENCE LISTING

<160> NUMBER OF SEQ ID NOS: 5

<210> SEQ ID NO 1
<211> LENGTH: 564
<212> TYPE: DNA
<213> ORGANISM: Mus musculus

<400> SEQUENCE: 1
atggttcgac cattgaactg catcgtcgcc gtgtcccaaa atatgggat tggcaagaac      60

| | |
|---|---|
| ggagacctac cctggcctcc gctcaggaac gagttcaagt acttccaaag aatgaccaca | 120 |
| acctcttcag tggaaggtaa acagaatctg gtgattatgg gtaggaaaac ctggttctcc | 180 |
| attcctgaga agaatcgacc tttaaaggac agaattaata tagttctcag tagagaactc | 240 |
| aaagaaccac cacgaggagc tcattttctt gccaaaagtt tggatgatgc cttaagactt | 300 |
| attgaacaac cggaattggc aagtaaagta gacatggttt ggatagtcgg aggcagttct | 360 |
| gtttaccagg aagccatgaa tcaaccaggc caccctcagac tctttgtgac aaggatcatg | 420 |
| caggaatttg aaagtgacac gttttttccca gaaattgatt tggggaaata taaacttctc | 480 |
| ccagaatacc caggcgtcct ctctgaggtc caggaggaaa aaggcatcaa gtataagttt | 540 |
| gaagtctacg agaagaaaga ctaa | 564 |

<210> SEQ ID NO 2
<211> LENGTH: 187
<212> TYPE: PRT
<213> ORGANISM: Mus musculus

<400> SEQUENCE: 2

```
Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185
```

<210> SEQ ID NO 3
<211> LENGTH: 564
<212> TYPE: DNA
<213> ORGANISM: Cricetulus griseus

<400> SEQUENCE: 3

| | |
|---|---|
| atggttcgac cgcttaactg catagtagca gtatcacaaa acatggggat agggaaaaat | 60 |
| ggggatcttc cgtggccgcc gttgcgtaac gaattcaaat acttccaacg tatgactact | 120 |
| acttcatcag tagaagggaa acaaaacctt gtaataatgg ggcgtaaaac atggttctca | 180 |
| ataccggaaa aaaccgtcc gcttaaagac cgtataaaca tagtactttc acgtgaactt | 240 |
| aaagaaccgc cgcgtggggc acattttctt gcaaaatcac ttgacgacgc acttcgtctt | 300 |

```
atagaacaac cggaacttgc atcaaaagta gacatggttt ggatagtagg ggggtcatca    360
gtataccaag aagcaatgaa ccaaccgggg caccttcgtc ttttcgtaac tcgtataatg    420
caagaattcg aatcagacac tttcttcccg gaaatagacc ttgggaaata caaacttctt    480
ccggaatacc cggggtatt gtcagaagta caagaagaaa aagggataaa atacaaattc    540
gaagtatacg aaaaaaaaga ctag                                           564

<210> SEQ ID NO 4
<211> LENGTH: 564
<212> TYPE: DNA
<213> ORGANISM: Cricetulus griseus

<400> SEQUENCE: 4
atggttcgac cgctaaactg catagtagcg gtatcgcaaa acatggggat agggaaaaat     60
ggggacttac cgtggccgcc gttacgaaac gaattcaaat acttccaacg tatgacgacg    120
acgtcgtcgg tagaagggaa acaaaaccta gtaataatgg ggcgtaaaac gtggttttcg    180
ataccggaaa aaaccgtcc gctaaaagac cgtataaaca tagtactatc gcgtgaacta    240
aaagaaccgc cgcgtggggc gcattttta gcgaaatcgc tagacgacgc gctacgtcta    300
atagaacaac cggaactagc gtcgaaagta gacatggttt ggatagtagg ggggtcgtcg    360
gtatatcaag aagcgatgaa ccaaccgggg cacttacgtt tattcgtaac gcgaataatg    420
caagaattcg aatcggacac gttcttcccg gaaatagacc tagggaaata caaactacta    480
ccggaatacc cggggtact atcggaagta caagaagaaa aagggataaa atacaaattc    540
gaagtatacg aaaaaaaaga ctag                                           564

<210> SEQ ID NO 5
<211> LENGTH: 564
<212> TYPE: DNA
<213> ORGANISM: Artificial Sequence
<220> FEATURE:
<223> OTHER INFORMATION: Consensus sequence

<400> SEQUENCE: 5
atggttcgac cgctdaactg catagtagcv gtatcvcaaa acatggggat agggaaaaat     60
ggggaccTac cgtggccgcc gttvcgdaac gaattcaaat acttccaacg tatgacbacd    120
acbtcdtcag tagaagggaa acaaaacctd gtaataatgg ggcgtaaaac vtggttctcv    180
ataccggaaa aaaccgtcc gctaaaagac cgtataaaca tagtacthtc dcgtgaacth    240
aaagaaccgc cgcgtggggc dcattttctt gcvaaatcdc tdgacgacgc vctacgtctt    300
atagaacaac cggaactdgc atcdaaagta gacatggttt ggatagtagg ggggtcdtcd    360
gtataccaag aagcvatgaa ccaaccgggg caccthcgtc thttcgtaac dcgdataatg    420
caagaattcg aatcdgacac gttcttcccg gaaatagacc tdgggaaata caaacttcth    480
ccggaatacc cggggtact vtcdgaagta caagaagaaa aagggataaa atacaaattc    540
gaagtatacg aaaaaaaaga ctag                                           564
```

METHODS FOR IMPROVING RECOMBINANT PROTEIN EXPRESSION

CROSS-REFERENCE TO RELATED APPLICATION

This application is the national stage entry of International Application No. PCT/US2010/044693 filed Aug. 6, 2010, which claims the benefit of priority to U.S. Provisional Application Ser. No. 61/231,906 filed Aug. 6, 2009, entitled "Methods for Improving Recombinant Protein Expression," the entire contents of which is are incorporated by reference herein.

FIELD OF INVENTION

This invention has practical application in the field of recombinant protein expression in eukaryotic cells by means of increasing selection pressure on a vector thereby increasing vector-associated heterologous protein expression.

BACKGROUND

In the field of recombinant protein production, increasing expression of a transfect gene is a fundamental priority during cell line development. Improving transcription, translation, protein folding and secretion are all targets of intense research to increase titers of the heterologous protein.

Regardless of methods used in the past, there exists a need in the art to provide better methods for recombinant protein production that increase yield of the desired protein.

SUMMARY OF THE INVENTION

In one aspect the invention provides a method for increasing heterologous protein expression in a host cell comprising the steps of culturing the host cell comprising a first heterologous polynucleotide sequence encoding the heterologous protein under conditions that allow for protein expression, the first polynucleotide encoded on a vector, the host cell further comprising a second polynucleotide sequence having a protein coding sequence for a selectable marker protein, the second polynucleotide having a sequence modification compared to a wild-type polynucleotide encoding the selectable marker protein, the sequence modification reducing translation efficiency of mRNA encoded by the second polynucleotide, the second polynucleotide having the sequence modification and the wild-type polynucleotide encoding identical amino acid sequences for the selectable marker protein. In one aspect, the first polynucleotide and the second polynucleotide are in a single vector, and in one embodiment of this aspect, the first polynucleotide and second polynucleotide are each under transcriptional control of distinct promoters. In other aspects, the first polynucleotide and the second polynucleotide are in separate vectors. In yet another aspect, the first polynucleotide and second polynucleotide are under transcriptional control of the same promoter.

In one embodiment of the method, the modification is in an untranslated region of the second polynucleotide encoding the selectable marker protein, and in certain aspects, the modification is in a 5' untranslated region and/or the modification is in a 3' untranslated region.

In another embodiment of the method, the modification is in a protein coding region of the gene encoding the selectable marker protein. In one aspect, the modification is within 25, 20, 15, 10, or 5 codons of an initiating codon of the protein coding region for the selectable marker gene coding sequence.

In another aspect of the method, the protein coding sequence in the second polynucleotide sequence comprises at least one modified codon that is not a wild-type codon in a wild-type polynucleotide encoding the selectable marker protein, the modified codon being a codon that is not a preferred codon for the encoded amino acid for the host cell. In one aspect, the protein coding sequence in the second polynucleotide sequence comprises at least one modified codon that is not a wild-type codon in a wild-type polynucleotide encoding the selectable marker protein, the modified codon being a codon that is a least preferred codon for the encoded amino acid for the host cell.

In another aspect of the method, the protein coding sequence in the second polynucleotide sequence comprises at least one modified codon that is not a wild-type codon in a wild-type polynucleotide encoding the selectable marker protein, and the modification introduces a change in secondary structure of the mRNA which reduces translation efficiency of the mRNA. In one embodiment of the method, the protein coding sequence in the second polynucleotide sequence comprises at least one modified codon that is not a wild-type codon in a wild-type polynucleotide encoding the selectable marker protein, and the modification increases codon pairing in the mRNA. In another embodiment of the method, the protein coding sequence in the second polynucleotide sequence comprises at least one modified codon that is not a wild-type codon in a wild-type polynucleotide encoding the selectable marker protein, and the modification modifies G+C content of the mRNA. In various aspects, the modification increases G+C content of the mRNA, and in various aspects, the G+C content is increased by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. In other aspects, the G+C content is increased by greater than 100%

In still another aspect of the method, the protein coding sequence in the second polynucleotide sequence comprises at least one modified codon that is not a wild-type codon in a wild-type polynucleotide encoding the selectable marker protein, and the modification modifies A+T content of the mRNA. In one embodiment, the modification decreases A+T content of the mRNA, and in certain aspects, the A+T content is decreased by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In other aspects of the method, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% of codons in the second polynucleotide protein coding sequence encoding the selectable marker protein are modified codons.

In still other aspects of the method, the selectable marker protein is selected from the group consisting of neomycin phosphotransferase (npt II), hygromycin phosphotransferase (hpt), dihydrofoate reductase (dhfr), zeocin, phleomycin, bleomycin resistance gene ble, gentamycin acetyltransferase, streptomycin phosphotransferase, mutant form of acetolactate synthase (als), bromoxynil nitrilase, phosphinothricin acetyl transferase (bar), enolpyruvylshikimate-3-phosphate (EPSP) synthase (aro A), muscle specific tyrosine kinase receptor molecule (MuSK-R), copper-zinc superoxide dismutase (sod1), metallothioneins (cup1, MT1), beta-lactamase (BLA), puromycin N-acetyl-transferase (pac), blasticidin acetyl transferase (bls), blasticidin deaminase (bsr), histidinol dehydrogenase (HDH), N-succinyl-5-aminoimidazole-4-carboxamide ribotide (SAICAR) synthetase (ade1), argininosuccinate lyase (arg4), beta-isopropylmalate dehydrogenase (leu2), invertase (suc2), orotidine-5'-phosphate (OMP) decarboxylase (ura3) and orthologs of any of these marker proteins.

In various embodiments of the method, the host cell is a eukaryotic cell, the host cell is a mammalian cell, the host cell is a human cell, the host cell is a Chinese hamster cell, the host cell is a Chinese hamster ovary cell, the host cell is a yeast cell, the host cell is *Saccharomyces cerevisiae* cell, the host cell is a *Pichia pastoris* cell, the host cell is a prokaryotic cell, the host cell is an *Escherichia coli* cell, the host cell is an insect cell, the host cell is a *Spodoptera frugiperda* cell, the host cell is a plant cell, or the host cell is a fungal cell.

In one aspect of the method, the expression vector is a (Chinese hamster elongation factor 1 (CHEF1) expression vector. In still another aspect, the method utilizes a second polynucleotide which comprises the polynucleotide set out in FIG. 2, and in one embodiment, the second polynucleotide comprises the polynucleotide set out in FIG. 2 in a (Chinese hamster elongation factor 1 (CHEF1) expression vector.

DESCRIPTION OF THE DRAWINGS

FIG. 1A is a DHFR-encoding polynucleotide (SEQ ID NO:1) and FIG. 1B is a DHFR polypeptide sequence (SEQ ID NO:2) used for codon deoptimization identical to *Mus musculus* cDNA BC005796.

FIG. 2 shows DNA sequences of the codon deoptimized DHFR sequences designated crippled (cr) (SEQ ID NO:3) and worst (wst) (SEQ ID NO:4).

FIG. 3 shows deoptimized DHFR (worst, wst (SEQ ID NO:4) and crippled, cr (SEQ ID NO:3) aligned with wild type (wt) (SEQ ID NO:1) sequence. Nucleotide changes (*) including hamster least preferred codons (see Table 4) and new tandem codon pairs (in bold; see Table 5) are indicated. Degenerate symbols in Contig[001] (SEQ ID NO:5) are: B (C or G or T), D (A or G or T), H (A or C or T), V(A or C or G).

FIG. 7 shows that codon deoptimized DHFR selected cells have reduced DHFR and increased protein of interest expression. CHO cells were transfected with wild type (T462) and codon deoptimized (pDEF81:FIGI, T463 and pDEF82:FIGI, T464) DHFR coexpressing the protein of interest FIGI. Transfection pools were stained with both fluorescent methotrexate (F-MTX) to detect DHFR and a fluorescent labeled antibody that recognizes FIGI (RPE). Stained cells were analyzed by flow cytometry on the FACSCalibur. FIG. 7A shows dual stain FACS profiles of 10,000 individual cells from each transfection plotting combined DHFR (F-MTX) and FIGI (RPE:FIGI) expression. FIG. 7B shows mean F-MTX (DHFR) and RPE fluorescence intensity from two populations of 10,000 cells averaged for each transfection. These results indicate that both codon deoptimized DHFR pools have reduced DHFR and increased FIGI production when compared to wild type cells.

FIG. 8A shows mean fluorescence of F-MTX stained cells. Each data point is an individual clone. Clones are ranked from low to high mean fluorescence. FIG. 8B shows mean fluorescence of RPE stained cells. Each data point is an individual clone. Clones are ranked from low to high mean fluorescence.

DETAILED DESCRIPTION OF THE INVENTION

Figure 4:
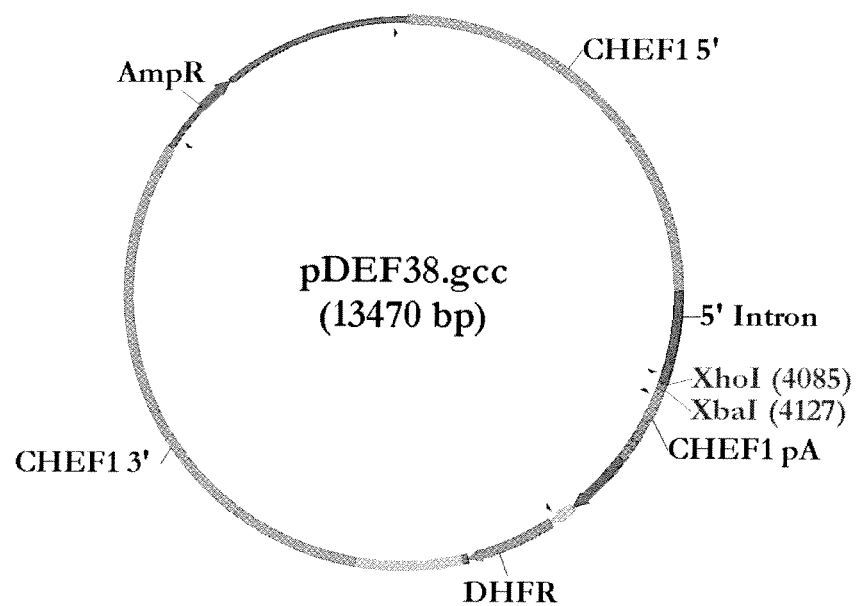
FIG. 4 shows the CHEF1 expression vector, pDEF38, with wild type (WT) DHFR. Codon deoptimized DHFR replaces WT DHFR to make pDEF81 (crippled DHFR) and pDEF82 (worst DHFR). The reporter gene FIGI is cloned into the XhoI-XbaI cloning sites to make pDEF38:FIGI, pDEF81:FIGI and pDEF82:FIGI.

The present invention provides a new generation of expression vectors and uses thereof, that improve recombinant protein yields. The vectors of the invention allow for increased expression of a gene of interest (GOI) in a host cell and reduce translation efficiency of a co-transformed selectable marker, thereby increasing selection stringency. Selectable markers are used in transfection experiments to complement host cell protein deficiencies or confer resistance to an otherwise toxic agent, and thereby select for the presence (expression) of co-transformed genes of interest. The vectors that provide for reduced translation efficiency of the selection marker protein are designed such that the polynucleotide encoding the selection marker protein are "deoptimized" with respect to one or more parameters. Use of the vectors provided is counterintuitive to materials and methods practiced for enhanced expression of recombinant proteins. Indeed, improved protein expression is typically effected by "optimizing" a polynucleotide encoding a protein of interest, thereby increasing translation efficiency and protein expression. By extension, one would optimize the protein coding region for the selectable marker gene in the same manner. Herein, however, it is unexpectedly shown that modifying a polynucleotide encoding a selectable marker gene sequence to be less than optimal for translation, regardless of making similar changes in the gene of interest, allows for isolation of host cells transformed or transfected with a polynucleoptide encoding a GOI and a polynucleotide encoding a selectable marker wherein the protein encoded by the GOI is expressed at unexpectedly high levels.

Accordingly, the term "deoptimized" as used herein with reference to a polynucleotide means that the polynucleotide has been modified in such a way that translation of a protein encoded by the polynucleotide is less than optimal for the host cell in which the polynucleotide has been introduced. A polynucleotide is deoptimized in a multitude of ways and the present invention is not limited by the methods exemplified herein.

Methods for codon optimization have been described by others (Itakura 1987, Kotula 1991, Holler 1993, Seed 1998). However, there are limited examples of codon deoptimization utility. One such example is the deoptimization of virus genes to reduce replicative fitness by incorporating least preferred codons or nonrandomized codon pairs (Burns 2006, Mueller 2006, Coleman 2008, Kew 2008). Herein is described the methodological considerations for reducing the translational efficiency of a dhfr gene for use in host cells by incorporating species-specific least preferred codons and tandem codon pairs. The methods presented are generally applicable to deoptimize codons in a polynucleotide encoding any selectable marker for its species specific host.

Without being bound by any particular mechanism of action, reduced translation of the selectable marker may lead to a compensatory increase in production of the same protein via an alternative pathway other than translation, such as, for example and without limitation, increased transcription or secretion, to enable survival of cells harboring the inefficient gene. Thus, those host cells which are able to overcome debilitation of the marker gene, and therefore survive, may also express the GOI at an increased rate. Regardless of the exact mechanism, it is unexpectedly shown herein that, contrary to conventional wisdom, modification of the polynucleotide sequence of the selectable marker gene in a way that reduces translational efficiency somehow increases expression of the co-transformed gene encoding the GOI.

The vectors and methods of the invention are amenable for use with any selectable marker gene that provides positive selection. Exemplary selectable markers include, without limitation antibiotic resistance genes encoding neomycin phosphotransferase (npt II), hygromycin phosphotransferase (hpt), dihydrofoate reductase (dhfr), zeocin, phleomycin, bleomycin resistance gene ble (enzyme not known), gentamycin acetyltransferase, streptomycin phosphotransferase, mutant form of acetolactate synthase (als), bromoxynil nitrilase, phosphinothricin acetyl transferase (bar), enolpyruvylshikimate-3-phosphate (EPSP) synthase (aro A), muscle specific tyrosine kinase receptor molecule (MuSK-R), copper-zinc superoxide dismutase (sod1), metallothioneins (cup1, MT1), beta-lactamase (HLA), puromycin N-acetyltransferase (pac), blasticidin acetyl transferase (bls), blasticidin deaminase (bsr), histidinol dehydrogenase (HDH), N-succinyl-5-aminoimidazole-4-carboxamide ribotide (SAICAR) synthetase (ade1), argininosuccinate lyase (arg4), Beta-isopropylmalate dehydrogenase (leu2), invertase (suc2) and orotidine-5'-phosphate (OMP) decarboxylase (ura3).

As is well understood in the art, the genetic code sets out codons that direct addition of specific amino acids in a translated polypeptide. As is also well understood in the art, the twenty naturally-occurring amino acids are encoded by different numbers of codons, ranging from one to six different codons for each amino acid. As used herein, different codons that encode the same amino acid are referred to as "synonymous codons." These synonymous codons are set out below in Table 1.

TABLE 1

The Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC Cys (C) |
| | TTA Leu (L) | TCA Ser (S) | TAA STOP | TGA STOP |
| | TTG Leu (L) | TCG Ser (S) | TAG STOP | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |

TABLE 1-continued

The Genetic Code

| T | C | A | G |
|---|---|---|---|
| GTA Val (V) | GCA Ala (A) | GAA Glu (E) | GGA Gly (G) |
| GTG Val (V) | GCG Ala (A) | GAG Glu (E) | GGG Gly (G) |

Because synonymous codons encode the same amino acid, altering the coding sequence of a protein by replacing a wild-type codon with a synonymous codon does not change the amino acid sequence of the encoded polypeptide sequence. However, the sequence of the underlying mRNA encoding the protein is altered and the change in the mRNA nucleotide sequence can alter gene expression by influencing translational efficiency (Ikemura 1981a, Ikemura 1981b, Ikemura 1985).

Specific factors that govern the efficiency of translation include incorporation of "preferred" codons, tandem or consecutive codons (Rosenberg 1993), codon pair bias (Gutman1989, Boycheva 2003), RNA secondary structure (Kozak 2005, Kudla 2009), GC content and nucleotide repeat structures (Hall 1982, Zhang 1991, Carlini 2003, Griswold 2003, Gustafsson 2004). Many of these factors result in, for example and without being bound by a specific mechanism, translation pause sites that not only stall translation but can affect protein folding kinetics, both ultimately altering protein expression. A well characterized example of translational pausing occurs during amino acid biosynthetic gene synthesis in bacteria and is widely known as attenuation (Watson 1988).

Codon Preference

In one aspect, the invention provides vectors and methods to increase expression of a recombinant protein encoded by a GOI, utilizing an expression vector comprising the GOI and also encoding a selectable marker protein in a synthetic polynucleotide designed with codons that are not preferred in the host cell. It is well known in the art that in different species, certain synomymous codons are more frequently utilized than others. Those codons that are most frequently utilized are referred to a "preferred codon" for that species. Others have proposed that preference for certain codons is a function of the relative number of specific transfer RNAs (tRNA) encoded in a species genome, and programs have been developed to determine the precise number of each tRNA encoded in a specific genome (Lowe and Eddy, 1997). Thus in one aspect, selection of less than preferred codons is based on previously determined utilization frequency of synonymous codons in a particular host cell species of origin.

In one aspect, the invention provides a polynucleotide encoding a selectable marker wherein the protein coding region of the polynucleotide includes at least one codon modification, the modification being replacement of a wild-type codon with a codon that is not a preferred codon for the host cell. In another aspect, the modification is replacement of a wild-type codon with a codon that is a least preferred codon for the host cell. Any number of such codon replacements is contemplated as long as a least one such modification is incorporated in the protein coding region. Accordingly, the invention contemplated anywhere from one such modified codon to modification of all codons in the protein coding region of the selectable marker gene.

More specifically, in various aspects at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% of codons in the protein coding sequence of the polynucleotide encoding the selectable marker gene are modified codons.

Using publicly available nucleotide sequences and codon usage tables, known in the art and exemplified as in Tables 2 and 3 (Nakamura et al., 2000) one can create a codon deoptimized version of any selectable marker by incorporating a random selection of least preferred codons for the species of origin of the host cell selected for expression of a recombinant protein encoded by the GOI. An example of the least preferred codons from hamster (*Cricetulus griseus*) are shown in Table 4. These codons are used to preferentially replace synonymous codons in a native gene sequence encoding a marker gene such that at least one to all of the synonymous codons are replaced with any codon that is not the preferred codon for a specific amino acid residue.

TABLE 2

Hamster Codon Usage Table
An example of a codon usage table from Hamster (*Cricetulus griseus*) from 331 protein coding regions and 153527 codons.
For each codon, the first number is the frequency per thousand and the second number is the actual number of times that codon was observed.

| UUU 19.6 (3005) | UCU 16.0 (2450) | UAU 13.1 (2017) | UGU 9.1 (1397) |
|---|---|---|---|
| UUC 22.0 (3381) | UCC 16.5 (2529) | UAC 16.4 (2519) | UGC 10.3 (1589) |
| UUA 6.4 (978) | UCA 10.3 (1577) | UAA 0.6 (93) | UGA 1.2 (177) |
| UUG 14.1 (2169) | UCG 3.4 (529) | UAG 0.5 (84) | UGG 13.1 (2012) |
| CUU 13.2 (2023) | CCU 16.7 (2563) | CAU 10.2 (1563) | CGU 5.6 (863) |

TABLE 2-continued

Hamster Codon Usage Table
An example of a codon usage table from Hamster (*Cricetulus griseus*) from 331 protein coding regions and 153527 codons. For each codon, the first number is the frequency per thousand and the second number is the actual number of times that codon was observed.

| | | | |
|---|---|---|---|
| CUC 18.4 (2818) | CCC 17.0 (2608) | CAC 12.9 (1980) | CGC 9.3 (1429) |
| CUA 7.6 (1174) | CCA 15.6 (2388) | CAA 10.3 (1587) | CGA 7.2 (1102) |
| CUG 38.8 (5955) | CCG 4.3 (657) | CAG 33.4 (5122) | CGG 10.1 (1558) |
| AUU 17.4 (2673) | ACU 14.1 (2172) | AAU 17.4 (2671) | AGU 11.4 (1756) |
| AUC 24.8 (3808) | ACC 20.3 (3118) | AAC 21.2 (3248) | AGC 16.4 (2521) |
| AUA 6.9 (1053) | ACA 15.7 (2418) | AAA 24.6 (3782) | AGA 10.1 (1557) |
| AUG 23.0 (3538) | ACG 4.5 (685) | AAG 38.4 (5895) | AGG 10.2 (1570) |
| GUU 11.6 (1780) | GCU 22.4 (3432) | GAU 24.6 (3781) | GGU 12.8 (1968) |
| GUC 15.7 (2408) | GCC 25.9 (3973) | GAC 28.1 (4310) | GGC 21.3 (3268) |
| GUA 7.8 (1202) | GCA 16.3 (2497) | GAA 28.4 (4355) | GGA 15.8 (2425) |
| GUG 30.1 (4628) | GCG 5.0 (765) | GAG 41.1 (6311) | GGG 13.4 (2063) |

TABLE 3

Human Codon Usage Table
Provided is an example of a codon usage table from Human (*Homo sapiens*) as determined from 93487 protein coding regions and analysis of 40662582 codons. For each codon, the first number is the frequency per thousand and the second number is the actual number of times that codon was observed.

| | | | |
|---|---|---|---|
| UUU 17.6 (714298) | UCU 15.2 (618711) | UAU 12.2 (495699) | UGU 10.6 (430311) |
| UUC 20.3 (824692) | UCC 17.7 (718892) | UAC 15.3 (622407) | UGC 12.6 (513028) |
| UUA 7.7 (311881) | UCA 12.2 (496448) | UAA 1.0 (40285) | UGA 1.6 (63237) |
| UUG 12.9 (525688) | UCG 4.4 (179419) | UAG 0.8 (32109) | UGG 13.2 (535595) |
| CUU 13.2 (536515) | CCU 17.5 (713233) | CAU 10.9 (441711) | CGU 4.5 (184609) |
| CUC 19.6 (796638) | CCC 19.8 (804620) | CAC 15.1 (613713) | CGC 10.4 (423516) |
| CUA 7.2 (290751) | CCA 16.9 (688038) | CAA 12.3 (501911) | CGA 6.2 (250760) |
| CUG 39.6 (1611801) | CCG 6.9 (281570) | CAG 34.2 (1391973) | CGG 11.4 (464485) |
| AUU 16.0 (650473) | ACU 13.1 (533609) | AAU 17.0 (689701) | AGU 12.1 (493429) |
| AUC 20.8 (846466) | ACC 18.9 (768147) | AAC 19.1 (776603) | AGC 19.5 (791383) |
| AUA 7.5 (304565) | ACA 15.1 (614523) | AAA 24.4 (993621) | AGA 12.2 (494682) |
| AUG 22.0 (896005) | ACG 6.1 (246105) | AAG 31.9 (1295568) | AGG 12.0 (486463) |
| GUU 11.0 (448607) | GCU 18.4 (750096) | GAU 21.8 (885429) | GGU 10.8 (437126) |
| GUC 14.5 (588138) | GCC 27.7 (1127679) | GAC 25.1 (1020595) | GGC 22.2 (903565) |
| GUA 7.1 (287712) | GCA 15.8 (643471) | GAA 29.0 (1177632) | GGA 16.5 (669873) |
| GUG 28.1 (1143534) | GCG 7.4 (299495) | GAG 39.6 (1609975) | GGG 16.5 (669768) |

TABLE 4

Hamster Least Preferred Codons
An example of the least preferred
codons from Hamster (*Cricetulus griseus*).

| Amino Acid | Least Preferred Codon |
|---|---|
| Alanine | GCG, GCA |
| Arginine | CGT, CGA, CGC |
| Aspartic Acid | GAT |
| Asparagine | AAT |
| Cysteine | TGT |
| Glutamic Acid | GAA |
| Glutamine | CAA |
| Glycine | GGT, GGG |
| Isoleucine | ATA, ATT |
| Histidine | CAT |
| Leucine | TTA, CTA, CTT |
| Lysine | AAA |
| Phenylalanine | TTT |
| Proline | CCG, CCA |
| Serine | AGT, TCG, TCA |
| Threonine | ACG, ACT |
| Tyrosine | TAT |
| Valine | GTA, GTT |

Codon deoptimization can be carried out by a variety of methods, for example, by selecting codons which are less than preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod'", "Drosophila_high.cod", "Human_high-.cod", "Maize_high.cod", and "Yeast_high.cod".

Codon Pair Bias

In another aspect, the invention provides vectors and methods to increase expression of a recombinant protein encoded by a transfected GOI, utilizing an expression vector encoding a selectable marker protein in a synthetic polynucleotide designed with codon pairs that are least favored in the host cell species of origin. Recent experimental results support the idea that translation rates are influenced by the compatabilities of adjacent tRNAs in the A- and P-sites on the surface of translating ribosomes (Smith and Yarus, 1989; Yarus and Curran, 1992). It is now understood that some codon pairs are used in protein coding sequences much more frequently than expected from the usage of the individual codons of these pairs (over-represented codon pairs), and that some codon pairs are observed much less frequently than expected (under-represented codon pairs). Coleman and others (2008) have shown that an underrepresented codon pair is translated slower than an overrepresented codon pair, and that the more under-represented a codon pair is, the slower it is translated.

By way of example, in humans, studies have shown that the Ala codon GCC is used four times as frequently as the synonymous codon GCG and that other synonymous codon pairs are used more or less frequently than expected (Coleman et al., 2008). This frequency of specific codon pairs is referred to as the "codon pair bias." For instance and again in humans, on the basis of preferred codon usage, the amino acid pair Ala-Glu is expected to be encoded by GCCGAA and GCAGAG about equally often. In fact, the codon pair GCCGAA is strongly underrepresented, even though it contains the most frequent Ala codon, such that it is used only one-seventh as often as GCAGAG.

Tandem Codon Pairing

In another aspect, the invention provides vectors and methods to increase expression of a recombinant protein encoded by a GOI, utilizing an expression vector comprising the GOI and also encoding a selectable marker protein in a synthetic polynucleotide designed with tandem codon pairing. The frequency and composition of codon pairs in a gene sequence can influence the rate of translation as evidenced by attenuation (Watson 1988) and translational frame shifting (Gurvich et al., 2005). The mechanism of attenuation involves the pausing of ribosomes at tandem pairs or multimeric repeats of the same codon and is influenced by the codon-specified activated tRNA concentration. When rare codons are paired the paucity of cognate tRNA molecules can lead to not only pausing, but frameshifting, resulting in a reduction of accurately translated protein. Both of these tandem codon pairing mechanisms of action could be utilized to deoptimize expression of a selectable marker gene.

Examples of hamster least preferred tandem codon pairs incorporated in the deoptimized dhfr genes are shown in Table 5.

TABLE 5

Tandem Codon Pairs

| Amino Acid | Tandem Codon Pairs |
|---|---|
| Aspartic Acid | GAC GAC |
| Glutamic Acid | GAA GAA |
| Glycine | GGG GGG |
| Leucine | CTA CTA |
| Lysine | AAA AAA |
| Phenylalanine | TTC TTC |
| Proline | CCG CCG |
| Serine | TCG TCG |
| Serine | TCA TCA |
| Threonine | ACG ACG |
| Threonine | ACT ACT |

Codons are all least preferred except those in bold

Thus, in one embodiment of the method, repeated amino acid residues in tandem in the selectable marker protein, wherein the same amino acid is present in more than one copy in the primary structure in tandem, are encoded by codons that are not a preferred codon for that amino acid. In another embodiment, repeated amino acid residues in tandem in the selectable marker protein, wherein the same amino acid is present in more than one copy in the primary structure in tandem are encoded by codons that are the least preferred codons for that amino acid. In another embodiment, the same amino acids present in more than one copy and in tandem in the primary structure are encoded by the same codon.

Secondary Structure

In another aspect, the invention provides methods to increase expression of a recombinant protein encoded by a GOI, utilizing an expression vector encoding a selectable marker protein in a polynucleotide designed with sequence modifications that alter RNA secondary structure.

In this embodiment, the structure of the mRNA is considered when designing a gene for codon deoptimization. The sequence context of, for example, the redesigned codons can modulate RNA secondary structure which has been shown to regulate the stability and translatability of the mRNA message (Griswold 2003, Kozak 2005, Kudla 2009). Factors to consider in designing a codon deoptimized selectable marker include, but are not limited to, secondary structure stability and minimum free energy (MFE) of the entire or 5' end of the RNA, as can be determined by open access RNA structure prediction software like RNAfold (Gruber et al., 2008).

Sequence context of the deoptimized gene in regions surrounding, or in part of a least preferred codon may also be important. Factors that may reduce translational efficiency include GC content, G+C in the codon third position (Sueoka and Kawanishi, 2000), and codon adaptation index scores (Sharp and Li, 1987). Indeed, evidence has shown that higher GC content in mRNA increases the likelihood of secondary structure formation that will hamper translation efficiency, and that reducing GC content destabilizes these secondary structures (Bulmer, 1989). Conversely then, in order to reduce translation efficiency as proposed by the instant methods, increasing GC content, either by replacing wild-type codons in the protein coding region with synonymous codons with higher GC content, or simply modifying untranslated regions to include a higher GC content, an increase in secondary structure is provided, thereby reducing the efficiency of translation.

It is well understood in the art that the primary and secondary structure of the mRNA 5' noncoding region modulate translational efficiency; translational efficiency has been shown to be inversely proportional to the degree of secondary structure at the mRNA 5' noncoding region. (Pelletier and Sonenberg, 1987). In another aspect, a method is provided wherein the polynucleotide encoding the selectable marker protein is modified outside of the context of the protein coding region, and modifications to the gene are made such that untranslated regions of the encoded mRNA have increased secondary structure compared to the wild-type mRNA. In one aspect, one or more modifications is introduced in a 5' and/or 3' untranslated region that is not necessary for translation. In another aspect, the modification or modifications are introduced in a 5' and/or 3' region that is necessary for translation.

Vectors and Host Cells

Any eukaryotic and prokaryotic vector is contemplated for use in the instant methods, including mammalian, yeast, fungal, insect, plant or viral vectors useful for selected host cell. The term "vector" is used as recognized in the art to refer to any molecule (e.g., nucleic acid, plasmid, or virus) used to transfer coding information to a host cell. The term "host cell" is used to refer to a cell which has been transformed, or is capable of being transformed, by a vector bearing a selected gene of interest which is then expressed by the cell. The term includes mammalian, yeast, fungal, insect, plant and protozoan cells, and the progeny of the parent cell, regardless of whether the progeny is identical in morphology or in genetic make-up to the original parent, so long as the selected gene is present. In general, any vector can be used in methods of the invention and selection of an appropriate vector is, in one aspect, based on the host cell selected for expression of the GOI.

Examples include, but are not limited to, mammalian cells, such as Chinese hamster ovary cells (CHO) (ATCC No. CCL61); CHO DHFR-cells, human embryonic kidney (HEK) 293 or 293T cells (ATCC No. CRL1573); or 3T3 cells (ATCC No. CCL92). Other suitable mammalian cell lines, are the monkey COS-1 (ATCC No. CRL1650) and COS-7 (ATCC No. CRL1651) cell lines, and the CV-1 cell line (ATCC No. CCL70). Still other suitable mammalian cell lines include, but are not limited to, Sp2/0, NS1 and NS0 mouse hybridoma cells, mouse neuroblastoma N2A cells, HeLa, mouse L-929 cells, 3T3 lines derived from Swiss, Balb-c or NIH mice, BHK or HaK hamster cell lines, which are also available from the ATCC.

Further exemplary mammalian host cells include primate cell lines and rodent cell lines, including transformed cell lines. Normal diploid cells, cell strains derived from in vitro culture of primary tissue, as well as primary explants, are also suitable.

Similarly useful as host cells include, for example, the various strains of *E. coli* (e.g., HB101, (ATCC No. 33694) DH5ÿ, DH10, and MC1061 (ATCC No. 53338)), various strains of *B. subtilis, Pseudomonas* spp., *Streptomyces* spp., *Salmonella typhimurium* and the like.

Many strains of yeast cells known to those skilled in the art are also available as host cells for expression of a GOI and include, for example, *Saccharomyces cerevisiae, Schizosaccharomyces pombe, Kluyveromyces* strains, *Candida, Pichia ciferrii* and *Pichia pastoris*.

Additionally, where desired, insect cell systems may be utilized in the methods of the present invention. Such systems include for example and without limitation, Sf-9 and Hi5 (Invitrogen, Carlsbad, Calif.).

Exemplary fungal cells include, without limitation, *Thermoascus aurantiacus, Aspergillus* (filamentous fungus), including without limitation *Aspergillus oryzaem, Aspergillus nidulans, Aspergillus terreus*, and *Aspergillus niger, Fusarium* (filamentous fungus), including without limitation *Fusarium venenatum, Penicillium chrysogenum, Penicillium citrinum, Acremonium chrysogenum, Trichoderma reesei, Mortierella alpina*, and *Chrysosporium lucknowense*.

Exemplary protozoan cells include without limitation *Tetrahymena* strains and *Trypanosoma* strains.

EXAMPLES

In one embodiment the present invention is exemplified using least-preferred hamster codons to generate a codon deoptimized DHFR (CDD) encoding-gene suitable for selection in Chinese hamster ovary (CHO) cells.

The starting gene was identical to a *Mus musculus* DHFR-encoding cDNA, Accession Number BC005796 and encodes the wild type DHFR polypeptide (See Figure)). Two versions of a codon deoptimized DHFR-encoding polynucleotide were synthesized, designated herein as crippled and worst, representing intermediate- and maximally-deoptimized coding sequences, respectively. These polynucleotides were designed using a GENEART AG CHO codon usage algorithm. The codon deoptimized DHFR-encoding polynucleotide sequences are shown in FIG. 2. The codon deoptimized DHFR genes are aligned with the wild type DHFR gene sequence in FIG. 3 and highlight the nucleotide differences resulting from the introduction of hamster least preferred codons and tandem codon pairs. The translation products for all three genes, wild type, crippled and worst, are identical.

The codon deoptimized DHFR-encoding polynucleotide sequences were introduced into expression vector pDEF38, a CHEF1 expression vector (U.S. Pat. No. 5,888,809), to replace the wild type DHFR encoding sequence (FIG. 4). The resultant plasmids were named pDEF81 (crippled DHFR) and pDEF82 (worst DHFR). The reporter gene of interest, FIGI, encoding an IgG1 Fc fusion protein, was cloned into the multiple cloning site (XhoI to XbaI) of pDEF38, pDEF81 and pDEF82 to create the expression vectors pDEF38:FIGI, pDEF81:FIGI and pDEF82:FIGI, respectively.

These FIGI expression vectors were transfected into CHO DG44 cells, grown for two days in non-selection media containing hypoxanthine and thymidine (HT), then selected in media lacking HT (-HT). The selected cell populations, or pools, were expanded and split into production model cultures to assess productivity.

Transfection pools were diluted to seed single cells into individual wells of 96 well plates. The plates were imaged with the Clone Select Imager (Genetix) and wells containing FIGI-expressing cells derived from a single cell were expanded. Twenty three clones were randomly selected from the limiting dilution plates for each transfection (wild type, crippled and worst DHFR) from the confirmed monoclonal sets.

The 6-well production models were inoculated with a total of one million cells into 3 ml of cell culture media with 10% FBS and grown for 4 days at 37° C., then 4 days at 34° C. Harvest supernatants were filtered through 0.2 micrometer filters and assayed for FIGI production by Protein A HPLC. Fed batch production models were seeded at 0.5 million cells/mL in culture media supplemented with 10% FBS in spin tubes. The 50 mL spin tubes were run with a working volume of 15 mL. After seeding, samples were grown at 37° C. and 6% $CO_2$ for 3 days, with feeding and temperature shift to 34° C. beginning on day 4. Samples for titer and cell densities were collected on days 3, 5, 7, 10 and 12. The study was concluded on day 12.

FACS analysis was performed with Day 2 normal growing cells that were harvested and stained with fluorescein isothiocyanate labeled methotrexate (F-MTX) to detect DHFR protein and an R-Phycoeythrin (RPE) labeled anti-IgG1 Fc to detect FIGI.

Stable cell lines expressing the reporter protein FIGI were made using wild type and codon deoptimized genes encoding the DHFR selectable marker. Duplicate transfections (T462-T464, A and B) were performed with the wild type, crippled and worst DHFR plasmids expressing the reporter protein FIGI. The individual colonies counted for each transfection are reported as "Number of Transfectants." As seen in the Table 6, the transfection results indicate that the selection pressure is increased when using codon deoptimized DHFR (CDD) as compared to wild type DHFR. This result is seen as a reduction in the number of CDD transfectants selected in media lacking HT.

TABLE 6

The number of transfectants per transfection.

| Transfection | Plasmid | DHFR Marker | Number of Transfectants |
| --- | --- | --- | --- |
| T462A | pDEF38:FIGI | Wild Type | 33834 |
| T462B | pDEF38:FIGI | Wild Type | 22663 |
| T463A | pDEF81:FIGI | Crippled | 1915 |
| T463B | pDEF81:FIGI | Crippled | 4309 |
| T464A | pDEF82:FIGI | Worst | 7342 |
| T464B | pDEF82:FIGI | Worst | 6863 |

Figure 5:
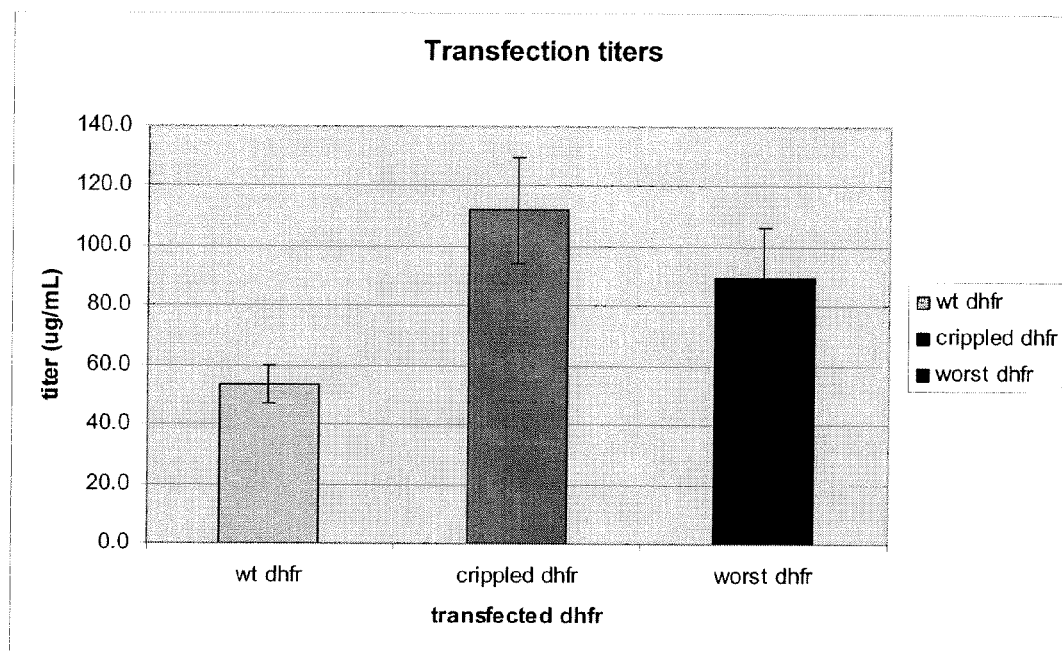
FIG. 5 shows that protein expression increases using codon deoptimized DHFR. CHO cells were transfected with wild type (wt) and codon deoptimized (crippled, pDEF81:FIGI and worst, pDEF82:FIGI) DHFR coexpressing a protein of interest (FIGI). Titer values determined by protein A HPLC and reported in μg/ml are averages of two independent transfections, each measured in triplicate (six total production assays). The results indicate a clear improvement in expression titer for the codon deoptimized DHFR selected transfection pools over the wild type DHFR pools.
Figure 6:
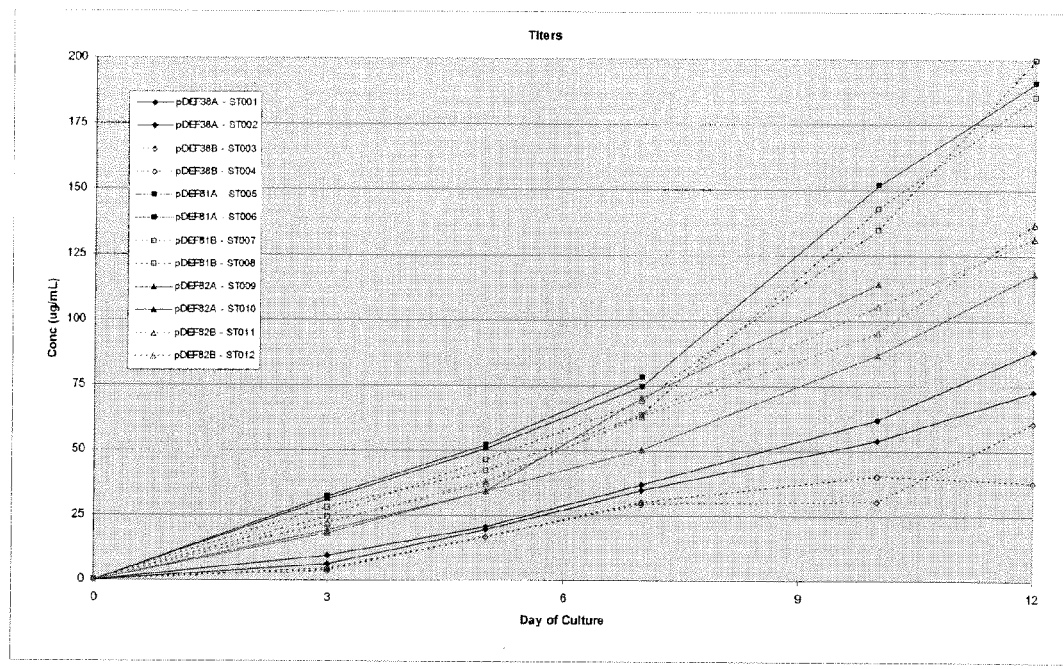
FIG. 6 demonstrates that a transfection pool fed-batch production model provides improved productivity in codon deoptimized cell lines. This experiment was carried out for 12 days in 50 ml spin tubes with pooled transfectants; wild type (pDEF38:FIGI, blue) and codon deoptimized (pDEF81:FIGI, purple and pDEF82:FIGI, pink) DHFR coexpressing the protein of interest FIGI. Two transfection pools (A and B) were done in duplicate. The codon deoptimized pools show greater productivity than the wild type samples.

The amount of FIGI protein produced from pooled transfectants in the 6-well, 8 day (FIG. 5) and spin tube, 12 day fed batch (FIG. 6) production models show an unexpected increase in productivity of the GOI with the codon deoptimized DHFR selectable marker gene over the wild type DHFR gene. The crippled DHFR gene yielded the highest titer. This result is consistent with the observation that the crippled DHFR selection was the most stringent (See Table 6) and suggests that the diversity in the population may be reduced but the average cell expresses more POI. This conclusion is evident in the crippled DHFR (T463) FACS distribution in FIG. 7A that shows a tight cluster of cells that stain brightly for RPE:FIGI with concomitant reduced F-MTX staining. The worst DHFR cells show a similar but broader RPE:FIGI staining pattern compared to crippled DHFR consistent with slightly lower titer in the production model. Compared to the wild type staining pattern, both codon deoptimized pools have a dramatic shift in staining with a reduction in DHFR and increased FIGI. This difference is more clearly seen in the increased mean fluorescence of the CDD pools over the wild type pool (FIG. 7B) and corroborates the conclusion that codon deoptimized DHFR selection results in increased POI production.

Figure 8:
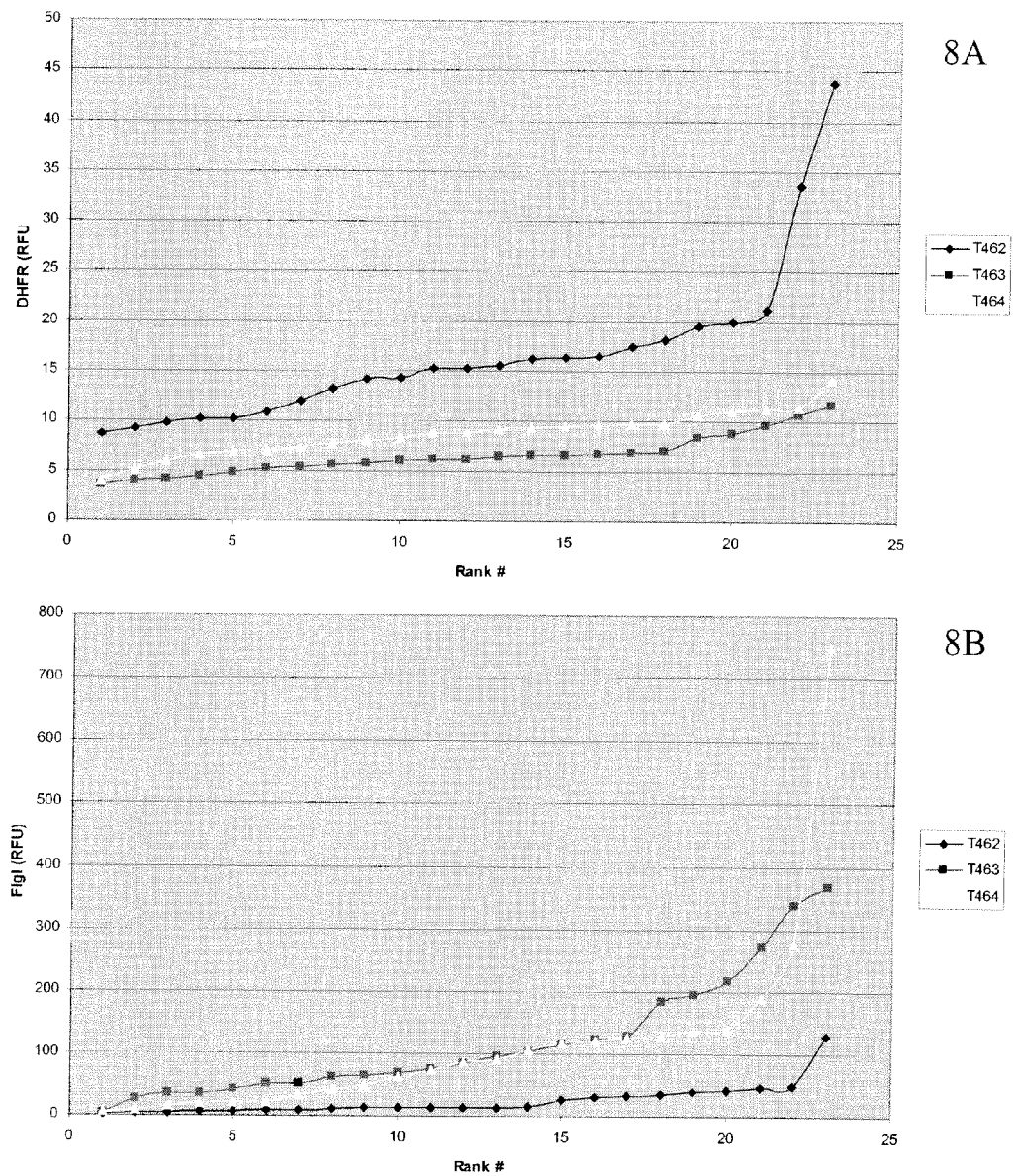
FIG. 8 demonstrates that codon deoptimized DHFR clones have reduced DHFR and increased protein of interest expression. CHO cell transfection pools (wild type T462, crippled T463 and worst T464) were cloned by limiting dilution and 23 confirmed monoclonal cell lines were expanded from each transfection. Clonal cells were stained with both fluorescent methotrexate (DHFR RFU) to detect DHFR and the RPE labeled anti-FIGI fluorescent antibody (FIGI RFU). A total of 10,000 stained cells from each clonal population were analyzed by flow cytometry on the FACSCalibur.
Figure 9:
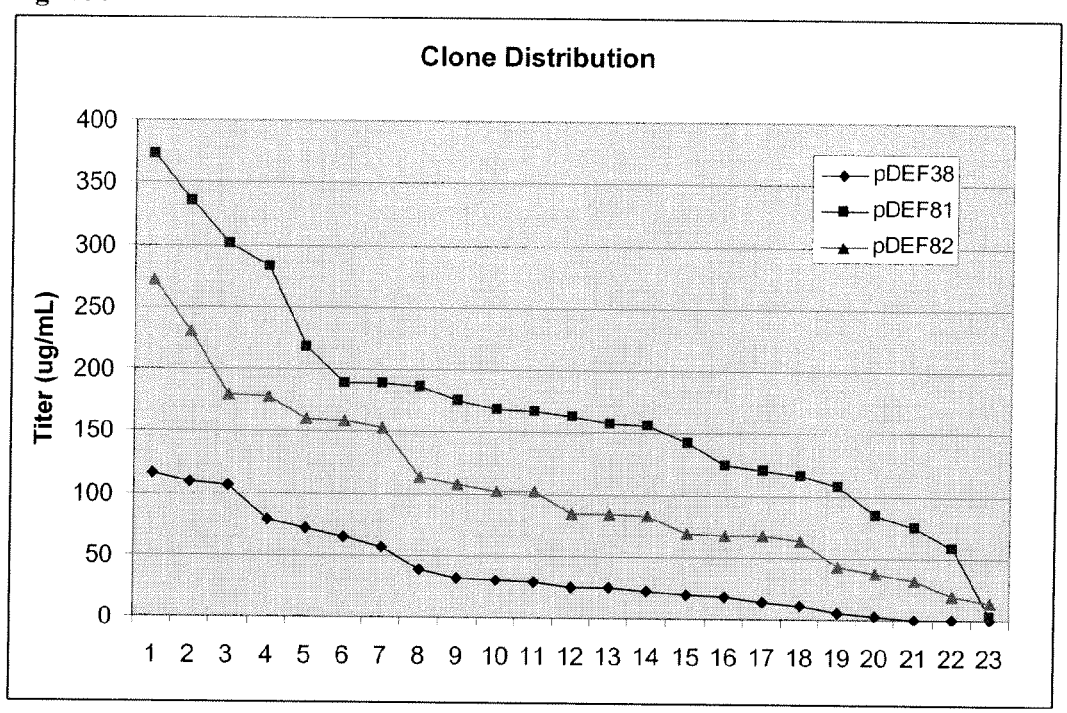
FIG. 9 shows that codon deoptimized clones have improved productivity compared to wild type clones. Clone titers were determined by Protein A HPLC on Day 8 harvest supernatants from 6-well production models. Clones are ranked by titer from high to low. The codon deoptimized clones, pDEF81:FIGI and pDEF82:FIGI, show greater FIGI productivity than the wild type DHFR clones (pDEF38:FIGI).

The observed increase in productivity with the CDD pools is further substantiated in the individual clones. Randomly selected clones were expanded then analyzed by flow cytometry and put into 6-well production model. The FACS profiles of the individual clones show that the codon deoptimized selected cells stain brighter for the POI (FIG. 8B) yet have lower DHFR levels (FIG. 8A) compared to the wild type DHFR sleeted clones. These data are consistent with the transfection pool data. Productivity of the clones in the Protein A assay are shown in FIG. 9 and demonstrate an increase in titer for random clones from the CDD selected pools. The titer differences for the CDD clones are between 2 and 3 times greater than the wild type.

All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept and scope of the invention. More specifically, it will be apparent that certain polynucleotides which are both chemically and biologically related may be substituted for the polynucleotides described herein while the same or similar results are achieved. All such similar substitutes and modifications apparent to those skilled in the art are deemed to be within the, scope and concept of the invention as defined by the appended claims.

The references cited herein throughout, to the extent that they provide exemplary procedural or other details supplementary to those set forth herein, are all specifically incorporated herein by reference.

What is claimed is:

1. A method for increasing heterologous protein expression in a mammalian host cell comprising the step of culturing the host cell under conditions that allow for protein expression, said host cell comprising a first heterologous polynucleotide sequence encoding said heterologous protein, said host cell further comprising a second polynucleotide sequence having a protein coding sequence for a selectable marker protein, said second polynucleotide having a sequence modification compared to a wild-type polynucleotide encoding said selectable marker protein, said sequence modification reducing translation efficiency of mRNA encoded by said second polynucleotide, said second polynucleotide having said sequence modification and said wild-type polynucleotide encoding identical amino acid sequences for said selectable marker protein, said first polynucleotide and said second polynucleotide encoded on a Chinese hamster elongation factor 1 (CHEF1) expression vector, wherein the second polynucleotide comprises the polynucleotide sequence of SEQ ID NO: 3 or SEQ ID NO: 4.

* * * * *